United States Patent
Kaufman

(10) Patent No.: US 6,380,380 B1
(45) Date of Patent: Apr. 30, 2002

(54) USE OF NICOTINAMIDE ADENINE DINUCLEOTIDE (NAD) AND NICOTINAMIDE ADENINE DINUCLIOTIDE PHOSPHATE (NADP) ANALOGS TO MEASURE ENZYME ACTIVITIES METABOLITES AND SUBSTRATES

(75) Inventor: Richard A. Kaufman, Bound Brook, NJ (US)

(73) Assignee: Specialty Assays, Inc., Manville, NJ (US)

( * ) Notice: Subject to any disclaimer, the term of this patent is extended or adjusted under 35 U.S.C. 154(b) by 0 days.

(21) Appl. No.: 09/475,736

(22) Filed: Dec. 30, 1999

Related U.S. Application Data

(60) Provisional application No. 60/114,610, filed on Jan. 4, 1999, now abandoned.

(51) Int. Cl.[7] ............... C07H 19/207; C12Q 1/58
(52) U.S. Cl. ............... 536/76.24; 435/12; 435/14; 435/15; 435/25; 435/26; 435/188
(58) Field of Search .............. 536/26, 24; 435/12, 435/14, 15, 25–26, 188

(56) References Cited

U.S. PATENT DOCUMENTS

| | | | |
|---|---|---|---|
| 4,250,254 A | | 2/1981 | Modrovich ............... 435/14 |
| 4,271,264 A | | 6/1981 | Modrovich ............... 435/14 |
| 4,372,874 A | | 2/1983 | Modrovich |
| 4,394,449 A | | 7/1983 | Modrovich ............... 435/188 |
| 5,037,738 A | | 8/1991 | Lamos et al. ............... 435/12 |
| 5,116,728 A | | 5/1992 | Crowther et al. ............... 435/14 |
| 5,124,141 A | * | 6/1992 | Makler ............... 424/7.1 |
| 5,141,854 A | | 8/1992 | Kaufman et al. ............... 435/26 |
| 5,278,044 A | | 1/1994 | San George et al. ......... 435/26 |
| 5,286,627 A | * | 2/1994 | Ueda et al. ............... 435/26 |
| 5,705,356 A | | 1/1998 | De Giorgio ............... 435/25 |
| 5,776,779 A | * | 7/1998 | Tamura et al. ............... 436/56 |
| 5,801,006 A | | 9/1998 | Kaufman ............... 435/15 |
| 5,804,403 A | | 9/1998 | Dorn et al. ............... 435/26 |
| 6,046,018 A | * | 4/2000 | Kozuma et al. ............... 435/26 |
| 6,068,989 A | | 5/2000 | Tanaka | |

FOREIGN PATENT DOCUMENTS

| | | | |
|---|---|---|---|
| DE | 40 38 306 A1 | * | 6/1991 |
| DE | 40 38 306 C2 | * | 5/1995 |
| EP | 0 387 697 | | 9/1990 |
| EP | 0 632 133 | | 1/1995 |
| EP | 0 639 646 | | 2/1995 |
| GB | 1397406 | * | 6/1975 |
| JP | 4-335899 A2 | * | 11/1992 |
| JP | 8-103298 A2 | * | 4/1996 |
| WO | WO 89/02925 | | 9/1987 |
| WO | WO 91/19974 | | 12/1991 |

OTHER PUBLICATIONS

*Biochemicals Organic Compounds and Diagnostic Reagents*(catalog), Sigma Chemical Company, St. Louis, MO, 1996 edition, only pp. 35 (see col. 2), 902 (see col. 2), 903 (see col. 1) and 994 (see col. 1) supplied.*

Anderson et al., "The Thionicotinamide Analogs of DPN and TPN. II. Enzyme Studies," *Biochemistry*, 2(5), 1017–1022 (Sep.–Oct., 1963).*

Ferrier, B., "An Enzymatic Cycling Method for 3–Acetylpryidine Adenine Dinucleotide to Increase the Sensitivity of Enzymatic Methods Which Employ This NAD Analog", Analytical Biochemistry 186, 229–232 (1990).

Minato, S., et al., "Application of Nicotinamide–Adenine Dinucleotide Analogs for Clinical Enzymology: A Spectrophotometric Method for Clinical Analysis of Lactate Dehyddrogenase Patterns with the Use of a Nicotinamide–Adenien Denucleotide Analog", Clinica Chimica Acta, 69 (1976) 243–249.

Florini, J., "Assay of Creatine Kinase in Microtiter Plates Using Thio–NAD to Allow Monitoring at 405nm", Analytical Biochemistsry 182, 399–404 (1989).

Hosaki, S., et al., "Simultaneous Determination of Multiple Forms of Lactate Dehydrogenase Based on NAD and Thio–NAD", Clinica Chimica Acta, 157 (1986) 321–322.

* cited by examiner

*Primary Examiner*—Gary Geist
*Assistant Examiner*—L. E. Crane
(74) *Attorney, Agent, or Firm*—Roberts & Mercanti LLP.

(57) ABSTRACT

Kits and methods for measuring enzyme activities and metabolites using NAD analogs and NADP analogs are disclosed. The analogs can be used as replacements for NAD and NADP cofactors in analytical procedures. Preferred aspects of the invention include kits containing the NAD analogs and NADP analogs for use in the measurement of ethanol, lactic acid, 3-hydroxybutyric acid, glucose, glycerol, triglycerides, alpha-glycerophosphate, bile acids, creatine kinase activity, glucose-6-phosphate dehydrogenase activity and lactic acid dehydrogenase activity in analytical samples.

13 Claims, No Drawings

US 6,380,380 B1

USE OF NICOTINAMIDE ADENINE DINUCLEOTIDE (NAD) AND NICOTINAMIDE ADENINE DINUCLIOTIDE PHOSPHATE (NADP) ANALOGS TO MEASURE ENZYME ACTIVITIES METABOLITES AND SUBSTRATES

CONTINUING APPLICATION DATA

This application claims the benefit of priority from provisional patent application No. 60/114,610, filed Jan. 4, 1999, now abandoned.

TECHNICAL FIELD

The invention is directed to the use of NAD analogs and NADP analogs as enzyme cofactors in the measurement of enzyme activities, metabolites and substrates using enzymatic procedures which require the use of NAD and/or NADP cofactors for their determination.

BACKGROUND OF THE INVENTION

NAD (nicotinamide adenine dinucleotide) and NADP (nicotinamide adenine dinucleotide phosphate) are enzyme cofactors which are widely used in the measurement of enzyme activities and metabolites. The popularity of these cofactors for analytical measurements arises from the fact that in their oxidized forms, i.e. NAD and NADP they have virtually no absorbance at wavelengths longer than about 320 nm. When they are reduced, for example during an enzyme or substrate assay, NADH and NADPH have absorbances in the ultraviolet region of the spectrum with a maximum at 340 nm. At this wavelength both reduced cofactors have a molar absorbtivity of $6.22 \times 10^3$. This unique property of the oxidized forms having virtually no absorbance at 340 nm and the reduced forms having a well defined absorbance maxima at 340 nm is the basis for their analytical use, especially in diagnostic test procedures.

Despite their popularity, these two cofactors are not without their shortcomings. One limitation is their somewhat weak oxidation potential, $E_o=-0.32$ for NAD and NADP (Lehniger, A. L., *Biochemistry*, Worth Publishers, Inc., New York, 1970). For many analytes and substrates this is not a serious problem, but for some substrates the reaction has to be "engineered" in order for it to proceed in the forward direction. An example of an "engineered" reaction is the enzymatic measurement of ethanol using alcohol dehydrogenase according to the following reaction.

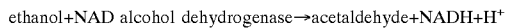
ethanol+NAD alcohol dehydrogenase→acetaldehyde+NADH+H⁺

To quantitatively measure ethanol in a sample the reaction needs to be at an alkaline pH, an excess of NAD has to be present and a means of removing the acetaldehyde must be incorporated into the reaction system to drive the reaction to completion. Typically a reactive primary amine e.g. 1,3-diamino-2-hydroxypropane is present to form a Schiff base with the acetaldehyde thereby removing it from solution (Kaufman et al., U.S. Pat. No. 5,141,854). The alkaline pH removes protons generated during ethanol oxidation which also helps drive the reaction in the forward direction. The alkaline pH, however, also brings with it other undesirable effects. NAD and NADP start to become unstable above pH 7 and their instability increases with increasing pH. In order to have an all liquid, single component reagent ready to use, with reasonable shelf life e.g. 18 months at 2° to 8° C., for measuring ethanol in analytical samples, the NAD must be stored in a separate container at a lower pH to maintain its stability. Thus at a minimum, a two vial reagent configuration is needed for an ethanol reagent to have reasonable shelf life stability. The NAD instability has been somewhat overcome by the addition of aliphatic zwitterionic secondary and tertiary amines, and maintaining the pH below 8 (Dorn et al., U.S. Pat. No. 5,804,403). But this technique still employs a two vial system which is more costly than single vial systems from both a labor and materials perspective. A trapping agent such as TRIS is also required to drive the reaction which further adds to costs. Other examples of metabolites which exhibit an unfavorable equilibrium for oxidation by NAD or NADP are glycerol, acetaldehyde, lactic acid and 3-hydroxybutyric acid.

A second limitation of NAD and NADP is their somewhat limited sensitivity. At 340 nm the molar absorbtivity of the reduced cofactors is $6.22 \times 10^3$. For most enzymes and metabolites measured by diagnostic procedures this is usually not a problem. With some diagnostic procedures, however, if a more sensitive cofactor were available better assay precision could be obtained or sample volumes could be reduced resulting in less interferences from endogenous serum sample components e.g. bilirubin, lipemia and hemoglobin. Examples of such clinical assays are the measurement of CK-MB activity which is an early and specific marker for patients having a myocardial infarction, some EST™ assays where the analyte is very low e.g. digoxin and tetrahydrocannabinol (THC) and the determination of serum steroids and bile acids which are present in serum at very low concentrations (EMIT is a registered trademark of Dade Behring Inc., Deerfield, Ill.).

A third limitation of NAD and NADP is the somewhat limited wavelengths at which the reduced cofactors absorb. In the near-UV region of the spectrum the reduced cofactors have their maximum absorbance at 340 nm. At longer wavelengths their absorbances fall off rapidly and at wavelengths longer than 400 nm they exhibit no absorbance at all. To develop assays based on the reduced cofactors where a colored product absorbs in the visible region of the spectrum is desired, formazon dyes and diaphorases have been used. Diaphorases catalyze the reduction of an oxidized formazon dye using a reduced cofactor according to the following reaction.

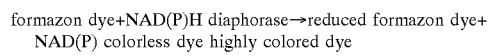
formazon dye+NAD(P)H diaphorase→reduced formazon dye+ NAD(P) colorless dye highly colored dye Assays for measuring serum triglycerides have been developed using formazon dyes to avoid the "clearing effect", which is observed at 340 nm, and is due to the decrease in turbidity in the reaction mixture as the triglycerides in the sample are hydrolyzed by lipase(s) to fatty acids and glycerol.

Thus, given the inherent limitations for NAD and NADP mentioned above, there exists a need for enzyme cofactors with more favorable oxidation potentials, broader absorbance spectra in the near-UV and visible regions of the spectrum, and with higher sensitivities than NADH and NADPH.

NAD analogs and NADP analogs overcome many of the limitations mentioned above regarding NAD and NADP. For example, depending on the analog, many have more favorable Eo values which would facilitate oxidation reactions at lower pH (Anderson et al., J. Biol. Chem. 221, 1219, 1959). Kaplan et al. (J. Biol. Chem., 221, 823, 1956) found that the equilibrium constant for oxidation of ethanol to acetaldehyde using 3-acetylpyridine-NAD was 200 hundred times more favorable than with NAD. The absorbance maxima, depending on the reduced analog, absorbs not only in the ultraviolet region of the spectrum but well into the visible region as well (Siegel et al., Arch. Biochem. Biophys. 82, 288, 1959, and Stein et al., Biochemistry 2, 5, 1963).

In addition to the reduced analogs having ultraviolet and visible absorbance properties they also, depending on the analog, have significantly higher molar absorbtivities (see Siegel et al. and Stein et al. above). Siegel et al. observed that the molar absorbtivities of 3-acetylpyridine-NADH at 363 nm was $9.1 \times 10^3$ and 3-pyridinealdehyde-NADH at 358 nm was $9.3 \times 10^3$. Stein et al. found the molar absorbtivity of reduced thionicotinamide adenine dinucleotide at 398 mn was $11.9 \times 10^3$ and the corresponding thio-NADPH analog at 399 nm was $11.7 \times 10^3$. For a more complete listing of molar absorbtivities of NADH and NADPH analogs see *Pyridine Nucleotide Coenzymes*, edited by David Poulson and Olga Arramovic, Coenzymes and Cofactors, Vol III, Part A, John Wiley, New York, 1987.

In some developed procedures using NAD and NADP, Ueda et al. (U.S. Pat. No. 5,780,256) used a two coenzyme cycling technique, where the reagent contained two coenzymes e.g. NAD(P) and thio-NAD(P), to measure ammonia, bile acids (U.S. Pat. No. 5,286,627) and 3-hydroxybutyric in biological samples. In these methods one coenzyme is continuously recycled between two dehydrogenase enzymes while the other coenzyme is continually reduced to increase assay sensitivity. In another procedure, Makler (U.S. Pat. No. 5,124,141) found 3-acetylpyridine-NAD to be useful for diagnosing the presence lactic acid dehydrogenase originating from Plasmodium falcipanum (malaria) in human serum since human lactic acid dehydrogenases are unable to reduce 3-acetylpyridine-NAD.

Further discussions of NAD and NADP and their analogs can be found in several reviews e.g. *The Pyridine Nucleotide Coenzymes*, edited by Everse et al., Academic Press, New York, 1982, and *Pyridine Nucleotide Coenzymes* referred to above.

Separately, commonly assigned U.S. Pat. No. 5,801,006 discloses diagnostic kits and methods of measuring various metabolites and enzyme activities using the reduced forms of NADH analogs and NADPH analogs. In the '006 patent, the reduced forms of the analogs demonstrate superior stability at pH's of from about neutral to about pH 9 and afford the artisan with the ability to replace many two vial assay systems with one vial systems. The '006 patent, however, is silent with regard to using the oxidized forms of the analogs in diagnostic tests. Furthermore, it could not be predicted from the '006 patent that the mere substitution of NAD analogs and NADP analogs for NAD and NADP would yield unexpected benefits such as being able to provide single vial assays for measuring compounds such as ethanol, lactic acid and 3-hydroxybutyric acid at pH's of from about 6 to 8.

SUMMARY OF THE INVENTION

In accordance with one aspect of the invention, the present invention includes a diagnostic reagent kit which includes a component of the formula: (I)

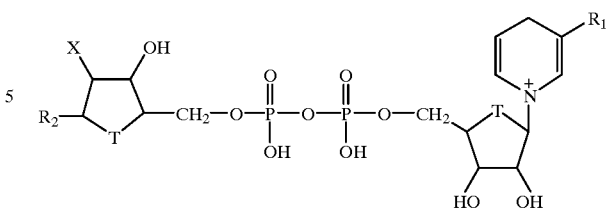

wherein:

$R_1$ is

$R_2$ is an aryl or heteroaryl;
Q is C or S;
T is O or S;
X is H. $OR_3$ or $H_2PO_4$, where $R_3$ is H, $C_{1-4}$ alkyl, $C_{1-4}$ haloalkyl, $C_{1-4}$ substituted alkyl or halogen;
Y is O, S or NOH; and
Z is H, $C_{1-6}$ alkyl, $C_{1-6}$ haloalkyl, $C_{1-6}$ substituted alkyl, NHL where L is H, OH, $NH_2$ aryl or aralkyl; except that L is not H when $R_2$ is adenine and Q is not S when Y is S.

In another preferred aspect of the invention, there is provided a method of quantifying the presence of an enzyme or analyte in a sample. The method includes:

a) contacting a sample with a compound of Formula I set forth above; and
b) measuring the change in absorbance or fluorescence resulting from said contacting step a).

Some preferred NAD analogs and NADP analogs which have been found to be useful for measuring enzyme activities and analytes using enzymes requiring these cofactors are 3-acetylpyridine adenine dinucleotide or 3-acetylpyridine-NAD; 3-acetylpyridine adenine dinucleotide phosphate or 3-acetylpyridine-NADP; 3-pyridinealdehyde adenine dinucleotide or 3-pyridine-aldehyde-NAD; 3-pyridinealdehyde adenine dinucleotide phosphate or 3-pyridinealdehyde-NADP; thionicotinamide adenine dinucleotide or thionicotinamide-NAD; and thionicotinamide adenine dinucleotide phosphate or thionicotinamide-NADP.

In preferred aspects of the invention, the NAD analogs and NADP analogs are included in kits and methods for determining the presence of metabolite or enzyme activities in an analytical sample. For example, glucose, triglycerides, bile acids, lactic acid, 3-hydroxybutyric acid, glycerol, α-glycerophosphate, ethanol, creatine kinase activity, lactate dehydrogenase activity and glucose-6-phosphate dehydrogenase activity (EMIT™ assays) can be determined in analytical samples using the analogs. One of the advantages of the present invention is that certain NAD analogs and NADP analogs such as 3-acetylpyridine-NAD, 3-acetylpyridine-NADP, 3-pyridinealdehyde-NAD, 3-pyridinealdehyde-NADP, thionicotinamide-NAD and thionicotinamide-NADP have more favorable oxidation potentials than NAD and NADP thus allowing oxidation of analytes by the analogs to proceed under conditions which is not feasible with NAD and NADP. For example oxidation reactions can often be carried out at a lower pH and often eliminating the need to remove one of the forward reaction products. Examples of such analytes are ethanol, lactic acid and 3-hydroxybutyric acid. The lower pH allows kits to be configured as ready-to-use single vial liquid reagents which simplifies the manufacturing process and makes reagents more convenient to use by the end user.

Another advantage of the analogs is that in their reduced form they have absorbances in the near-UV and also in the visible region of the spectrum. For example the reduced analogs 3-acetylpyridine-NADH, 3-acetylpyridine-NADPH, 3-pyridinealdehyde-NADH, and 3-pyridinealdehyde-NADPH have appreciable absorbances at 405 nm with molar absorbtivities of approximately $2 \times 10^3$. Thionicotinamide-NADH and thionicotinamide-NADPH have absorbance maxima at 398 nm with molar absorbtivities of about $11.9 \times 10^3$.

A third advantage of certain NAD analogs and NADP analogs is the increased sensitivity of the reduced forms compared with NADH and NADPH. For example 3-acetylpyridine-NADH, 3-acetylpyridine-NADPH have absorbance maxima at 363 nm with molar absorbtivities of $9.4 \times 10^3$ which at this wavelength is 1.5 times more sensitive than NADH and NADPH at their absorbance maxima at 340 nm which is $6.22 \times 10^3$. Similarly 3-pyridinealdehyde-NADH has absorbance maxima at 358 nm with a molar absorbtivity of $9.9 \times 10^3$. As mentioned above the thionicotinamide analogs have sensitivities at 398 nm nearly twice NADH and NADPH at 340 nm. For enzyme and analyte assays requiring increased sensitivity, the analogs provide approximately 1.5 to 2 fold increased sensitivity and at longer wavelengths which also reduces spectral interference form e.g. endogenous sample interferrents such as lipemia (triglycerides), bilirubin and hemoglobin found in serum.

One of the advantages of the methods of the present invention is that they allow the artisan to measure various metabolites at pH ranges around slightly acidic, neutral to slightly alkaline e.g. up to pH 8.0 or greater when compared to NAD or NADP. Thus, economical single vial systems can be prepared.

DETAILED DESCRIPTION OF THE INVENTION

In one preferred aspect the invention is directed to diagnostic kits containing NAD analogs and NADP analogs. The analogs are of the Formula: (I)

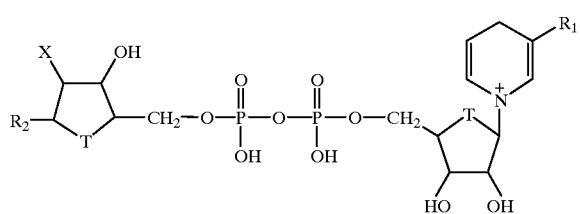

wherein:

$R_1$ is

$R_2$ is an aryl or heteroaryl;
Q is C or S;
T is O or S;
X is H, $OR_3$ or $H_2PO_4$, where $R_3$ is H, $C_{1-4}$ alkyl, $C_{1-4}$ haloalkyl, $C_{1-4}$ substituted alkyl or halogen;

Y is O, S or NOH; and
Z is H, $C_{1-6}$ alkyl, $C_{1-6}$ haloalkyl, $C_{1-6}$ substituted allyl, NHL where L is H, OH, $NH_2$ aryl or aralkyl; except that L is not H when $R_2$ is adenine and Q is not S when Y is S.

Within Formula (I), $R_1$ is preferably selected from among the group:

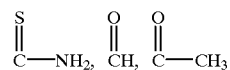

Alternatively, $R_1$ can be selected from among:

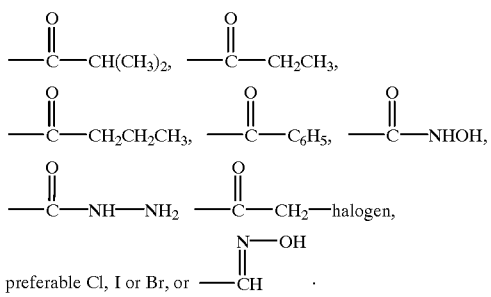

preferable Cl, I or Br, or —CH

Preferably, $R_2$ is a an adenine such as

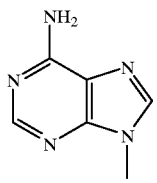

Alternatively, $R_2$ can be a substituted adenine, a substituted or unsubstituted member of the group consisting of xanthines, thioxanthines, hypoxanthines, guanines or other fused heterocyclic ring structures, aryls, substituted aryls, etc.

Also within Formula (I), X is preferably OH or $H_2PO_4$ and each T is O. Preferred compounds for inclusion with the kits and methods describe herein in accordance with Formula (I) include 3-acetylpyridine-NAD, 3-acetylpyridine-NADP, 3-pyridinealdehyde-NAD, 3-pyridinealdehyde-NADP, thionicotinamide-NAD and thionicotinamide-NADP. These compounds can be synthesized using standard organic chemistry techniques, or, if desired, purchased from commercial suppliers such as Sigma Chemical Co. It is contemplated that the kits of the present invention will include the compounds of Formula (I) in amounts ranging from about 0.01 to about 10 mmol/L.

The kits and methods of the present invention are useful in the measurement of various enzyme activities and analytes. A non-limiting list of such materials, such as substrates or metabolites and enzyme activities, which can be measured using the analogs described herein include creatine kinase, glucoses-6-phosphate dehydrogenase (EMIT™ assays), lactate dehydrogenase, ethanol, glucose, glycerol, α-glycerophosphate, triglycerides, bile acids, lactic acid and 3-hydroxybutyric acid.

In additional aspects of the invention, the diagnostic kits also may include an enzyme such as NAD and/or NADP-dependent enzymes. A non-limiting list of such enzymes includes lactate dehydrogenase, alcohol dehydrogenase, 3-hydroxybutyric acid dehydrogenase, glucose dehydrogenase, and glucose-6-phosphate dehydrogenase, α-glycerophosphate dehydrogenase and 3-α-hydroxysteroid dehydrogenase. Other enzymes will be apparent to those of ordinary skill. The enzymes will be present in sufficient amounts to provide enzyme activities from about 0.05 to about 150 Units/ml of reagent containing solution. It will be understood that the actual amounts of enzyme activity will depend upon the enzyme(s) included in the kit and target metabolite or enzyme activity sought to be measured.

Since the NAD/NADP analogs of Formula (I) are not the "natural" cofactors commonly found in biological systems, the functionality of the analogs with dehydrogenase enzymes must be determined.

The kits of the present invention can be prepared in either wet or dry form, including lyophilized form, depending upon the needs of the user. The kits can also include a suitable buffer such as tris(hydroxymethyl)aminomethane, [3-(N-morpholino)-2-hydroxypropane-sulfonic acid] and trapping compounds such as primary and secondary amines, and diamines which may interact with aldehyde and ketone groups formed during oxidation of hydroxyl groups. The purpose of having trapping compounds is to drive the reaction towards completion by removing one of the end products from the reaction. It will be apparent to those of ordinary skill in the art that the buffer included will depend upon the preference of the artisan and will also be selected based on the metabolite or enzyme activity sought to be measured. It is contemplated, however, that there will be sufficient buffer in the kits, i.e. from about 0.01 to about 1.0 mol/liter, and the analog containing solution will have a pH of from about 5 to 10. Also the trapping compounds which may be used for metabolites such as lactic acid, 3-hydroxybutyric acid, glycerol, α-glycerophosphate and ethanol will be used at concentrations sufficient to drive the reaction far enough in the forward direction to obtain the desired assay dynamic range. Concentrations will range from about 0.01 mol/liter to about 1.0 mol/liter. A competitive enzyme inhibitor such as pyrazole may be added to the ethanol reagent to extend the dynamic range of the assay.

In still further aspects of the invention, the diagnostic kits can contain a substrate such as creatine phosphate, adenosine-5'-diphosphate, glucose, glucose-6-phosphate, lactic acid and adenosine triphosphate. The substrates will be present in amounts from about 0.1 mmol/liter to about 1000 mmol/liter. If desired, the kits can be prepared to include a suitable antimicrobial such as sodium azide, Kathon, Bronopol or parabens. Such antimicrobials can be present in amounts ranging from about 0.01 to about 0.5% by wt.

Reagents in accordance with the present invention can be configured in several different formats. A single vial may be prepared which contains all necessary components including an antimicrobial, buffer, and components to stabilize the coupling enzyme(s), if present. For convenience, a single vial ready-to-use liquid reagent is preferred with a storage temperature of about +2° to +8° C. (refrigerator storage). Alternatively, the reagents may be prepared as a two component system or even a three or more component system and as powder (dry-fill) or lyophilizate. Having components of the reagent in separate vials or bottles usually results in better component stability, but may be deemed less convenient by some end users.

EXAMPLES

The following non-limiting examples illustrate certain aspects of the invention. All parts and percentages are by weight unless otherwise noted and all temperatures are in degrees Celsius. The principal chemicals were obtained from commercial suppliers such as Sigma Chemical Co. and all NAD analogs and NADP analogs were produced by Specialty Assays Inc.

The reagent compositions given below are the final concentrations after taking into account the sample volume. It is understood that the reagents can be made with varying degrees of concentration. For example, a concentrated version of the reagent can be prepared and then diluted with distilled, deionized, purified or non-purified water before the reagent is used.

1. Determination of Ethanol

The following is an example of a reagent composition for the determination of ethanol in an analytical sample using 3-acetylpyridine-NAD. Ethanol is measured using the following reaction:

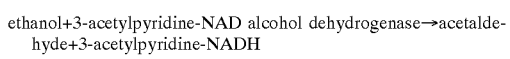
ethanol+3-acetylpyridine-NAD alcohol dehydrogenase→acetaldehyde+3-acetylpyridine-NADH In this reaction, oxidation of ethanol by 3-acetylpyridine-NAD is catalyzed by alcohol dehydrogenase to produce acetaldehyde and 3-acetylpyridine-NADH. The determination of ethanol in analytical samples is conveniently determined using the above reaction using a rate assay, where the rate of formation of 3-acetylpyridine-NADH is conveniently monitored at any wavelength between about 310 and 420 nm over a specified time interval. The oxidized form of 3-acetylpyridine-NAD has essentially no absorbance over these wavelengths while the reduced form has a maximum absorbance at 363 nm. Ethanol was determined on a COBAS MIRA™ (Roche Diagnostic Systems, Indianapolis, Ind.) at 37° C. using a rate assay, where after 2 ul sample and 10 ul water were mixed with 200 ul reagent the Δabsorbance/min at 340 nm was determined over the time interval from about 10 seconds to about 240 seconds.

The reagent composition was as follows:

| Ingredient | Concentration | Acceptable |
|---|---|---|
| [3-(N-morpholino)-2-hyroxypropane-sulfonic acid] (MOPSO) | 0.094 mol/liter | 0.01 to 3 mol/liter |
| pyrazole | 3.8 mmol/liter | 0 to 40 mmol/liter |
| N-hydroxyethylethylenediaminetriacetic acid, trisodium salt (HEDTA) | 1 mmol/liter | 0 to 20 mmol/liter |
| 3-acetylpyridine-NAD | 0.94 mmol/liter | 0.1 to 10 mmol/liter |
| bovine serum albumin | 0.094% | 0 to 5% |
| alcohol dehydrogenase | 94 Units/ml | >10 Units/ml |
| sodium azide | 0.075% | 0 to 1% |
| xylitol | 9.4% | 0 to 40% |
| pH | 7.2 | 6 to 10 |

To perform the ethanol assay a 200 mg/dL ethanol standard was used and aqueous ethanol standards from 25 to 600 mg/dL were assayed and recoveries compared with the standard values. Results were as follows:

| Ethanol Standard (mg/dL) | Ethanol Recovered (mg/dL) |
|---|---|
| 25 | 22 |
| 50 | 48 |
| 100 | 101 |

| Ethanol Standard (mg/dL) | Ethanol Recovered (mg/dL) |
|---|---|
| 200 | 204 |
| 400 | 391 |
| 600 | 590 |

Calibration Factor on COBAS MIRA 9826

If desired a trapping compound, such as TRIS or other primary amines or primary diamines can be added to remove the acetaldehyde. Also other pyrazole derivatives and heavy metal chelators such as citrate salts may be used in place of pyrazole and HEDTA.

Determination of Lactic Acid

The following is an example of a reagent composition for the determination of lactic acid in analytical samples using 3-acetylpyridine-NAD. Lactic acid is measured using the following reaction:

lactic acid+3-acetylpyridine-NAD lactic acid dehydrogenase→pyruvic acid+3-acetylpyridine-NADH In this reaction lactic acid dehydrogenase catalyzes the oxidation of lactic acid by 3-acetylpyridine-NAD to pyruvic acid and 3-acetylpyridine-NADH. The determination of lactic acid in analytical samples is conveniently determined using the above reaction using an end point assay, where reduced 3-acetylpyridine-NADH is conveniently monitored at any wavelength between about 310 and 420 nm. Lactic acid was determined on a COBAS MIRA™ at 37° C. using a 10 min end point assay, where the change in absorbance at 340 nm was determined before and after 2 ul sample and 18 ul water were added to 180 ul reagent.

The reagent composition was as follows:

| Ingredient | Concentration | Acceptable |
|---|---|---|
| 1,3-diamino-2-hydroxypropane | 0.09 mol/L | 0.01 to 2 mol/L |
| lactic acid dehydrogenase (porcine heart) | 9 U/L | >1 U/L |
| bovine serum albumin | 0.1% | 0 to 5% |
| 3-acetylpyridine adenine dinucleotide | 1 mmol/L | >0.1 mmol/L |
| pH | 8.0 | 6 to 10 |
| sodium azide | 0.1% | 0 to 1% |

To perform the lactic acid assay a 5 mmol/L lactic acid standard was used and aqueous lactic acid standards from 1.0 to 20 mmol/L were assayed and recoveries compared with the standard values. Results were as follows:

| Lactic Acid Standard (mmol/L) | Lactic Acid Recovered (mmol/L) |
|---|---|
| 1.0 | 0.9 |
| 2.5 | 2.3 |
| 5.0 | 5.0 |
| 10.0 | 10.3 |
| 15.0 | 15.1 |
| 20.0 | 19.6 |

Calibration Factor on COBAS MIRA: 31.8

Other buffers can be used. In the example above, 1,3 diamino-2-hydroxypropane was the buffer which reacts with pyruvic acid and helps drive the reaction in the forward direction. Other primary amine and primary diamine buffers can also be used such as TRIS, ethylenediamine, and 1,3-diaminopropane etc.

3. Determination of 3-Hydroxybutyric Acid

The following is an example of a reagent composition for the determination of 3-hydroxybutyric acid in an analytical sample using 3-pyridinealdehyde-NAD. 3-Hydroxybutyric acid is measured using the following reaction:

3-hydroxybutyric acid+3-pyridinealdehyde-NAD 3-hydroxybutyrate dehydrogenase→acetoacetic acid+3-pyridinealdehyde-NADH In this reaction, oxidation of 3-hydroxybutyric acid by 3-pyridinealdehyde-NAD is catalyzed by 3-hydroxybutyrate dehydrogenase to produce acetoacetic acid and 3-pyridinealdehyde-NADH. The determination of 3-hydroxybutyric acid in analytical samples is conveniently determined using the above reaction using an end point assay, where the reduction of 3-pyridinealdehyde-NAD is conveniently monitored at any wavelength between about 310 and 420 nm over a specified time interval. 3-Hydroxybutyric acid was determined on a COBAS MIRA™ at 37° C. using an end point assay, where the increase in absorbance at 340 nm was monitored from about 4.5 seconds after mixing 10 ul sample and 10 ul water with 200 ul reagent and the reaction carried out to 10 minutes.

The reagent composition was as follows:

| Ingredient | Concentration | Acceptable |
|---|---|---|
| tris(hydroxymethyl)aminomethane | 0.10 mol/L | 0.01 to 3 |
| bovine serum albumin | 0.1% | 0 to 5% |
| 3-pyridinealdehyde-NAD | 4 mmol/L | >0.5 mmol/L |
| pH | 8.0 | 6 to 10 |
| sorbitol | 10% | 0 to 30% |
| sodium azide | 0.08% | 0 to 1% |
| 3-hydroxybutyric acid dehydrogenase | 1500 U/L | >100 U/L |

To perform the 3-hydroxybutyric acid assay a 4 mmol/L D(-)3-hydroxybutyric acid standard was used and aqueous D(-)3-hydroxybutyric acid standards from 1.0 to 10.0 mmol/L were assayed and recoveries compared with the standard values. Results were as follows:

| D(-)3-hydroxybutyric Standards (mmol/L) | D(-)3-hydroxybutyric Recovered (mmol/L) |
|---|---|
| 1.0 | 1.0 |
| 2.0 | 2.0 |
| 4.0 | 4.0 |
| 7.0 | 7.0 |
| 10.0 | 10.0 |

Calibration Factor on COBAS MIRA: 13.5

Other buffers may be used which adequately buffer the reaction mixture.

4. Determination of Glucose with Glucose Dehydrogenase

The following is an example of a reagent composition for the determination of glucose in an analytical sample using 3-pyridinealdehyde-NAD and glucose dehydrogenase. Glucose is measured using the following reaction:

β-D-glucose+3-pyridinealdehyde-NAD glucose dehydrogenase→D-glucono-δ-actone+3-pyridinealdehyde-NADH In this reaction, oxidation of β-D-glucose by 3-pyridinealdehyde-NAD is catalyzed by glucose dehydrogenase to produce D-glucono-δ-lactone and 3-pyridinealdehyde-NADH. The determination of glucose in analytical samples is conveniently determined using the above reaction using a fixed-point assay, where the reduction of 3-pyridinealdehyde-NAD is conveniently monitored at any wavelength between about 310 and 420 nm over a specified time interval.

Glucose was determined on a COBAS MI RA™ at 37° C. using a fixed-point assay where the Δabsorbance at 340 nm was determined over the time interval from 4.5 seconds after mixing 2 ul sample and 20 ul water with 200 ul reagent and out to about 240 seconds.

The reagent composition was as follows:

| Ingredient | Concentration | Acceptable |
|---|---|---|
| tris(hydroxyamino)methane | 0.10 mol/L | 0.01 to 2 |
| bovine serum albumin | 0.1% | 0 to 5% |
| 3-pyridinealdehyde-NAD | 1 mmol/L | >0.1 mmol/L |
| pH | 7.5 | 6 to 10 |
| sodium azide | 0.03% | 0 to 1% |
| glucose dehydrogenase (Amano Enzyme U.S.A. Co., Ltd. Route 2, Box 1475, Troy, VA 22974) | 250 U/L | >50 U/L |

To perform the glucose assay a 250 mg/dL standard was used and aqueous glucose standards from 100 to 1500 mg/dL were assayed and recoveries compared with the standard values. Results were as follows:

| Glucose Standards (mg/dL) | Glucose Recovered (mg/dL) |
|---|---|
| 100 | 99 |
| 250 | 254 |
| 500 | 541 |
| 1000 | 1010 |
| 1500 | 1509 |

Calibration Factor on COBAS MIRA: 4803

Other buffers may be used which adequately buffer the reaction mixture.

5. Determination of Glucose using Hexokinase and Glucose-6-Phosphate Dehydrogenase The following is an example of a reagent composition for the determination of glucose in an analytical sample using thionicotinamide-NAD and Hexokinase/glucose-6-phosphate dehydrogenase. Glucose is measured using the following reaction:

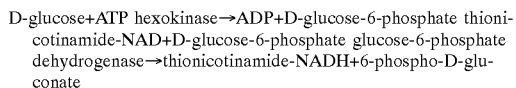

D-glucose+ATP hexokinase→ADP+D-glucose-6-phosphate thionicotinamide-NAD+D-glucose-6-phosphate glucose-6-phosphate dehydrogenase→thionicotinamide-NADH+6-phospho-D-gluconate In this reaction, D-glucose is phosphorylated by ATP (adenosine 5'-triphosphate) in the presence of hexokinase to form glucose 6-phosphate. Glucose 6-phosphate is then oxidized by thionicotinamide-NAD in the presence of glucose-6-phosphate dehydrogenase to form thionicotinamide-NADH. The determination of glucose in analytical samples is conveniently determined using an end point assay where the reduction of thionicotinamide-NAD is conveniently monitored at any wavelength between about 360 and 450 nm over a 175 second time period after mixing sample with reagent. Glucose was determined on a COBAS MIRA™ at 37° C. at 405 nm using an end point assay where the Δabsorbance was determined about 175 seconds after adding 2 ul sample and 20 ul water to 200 ul reagent.

le;.5qThe reagent composition was as follows:

| Ingredient | Concentration | Acceptable |
|---|---|---|
| tris(hydroxyamino)methane | 0.10 mol/L | 0.01 to 2 |
| hexokinase | 1000 U/L | >100 U/L |
| glucose 6-phosphate dehydrogenase | 1000 U/L | >100 U/L |
| ATP (adenosine 5'-triphosphate) | 2 mmol/(L | 0.1 mmol/L |
| magnesium sulfate | 5 mmol/L | 0.5 mmol/L |
| bovine serum albumin | 0.1% | 0 to 5% |
| thionicotinamide-NAD | 1 mmol/L | >0.1 mmol/L |
| pH | 7.5 | 6 to 10 |
| sodium azide | 0.085% | 0 to 1% |

To perform the glucose assay a 250 mg/dL standard was used and aqueous glucose standards from 100 to 500 mg/dL were assayed and recoveries compared with the standard values. Three uls sample and 20 uls water were added to 200 uls reagent. Results were as follows:

| Glucose Standards (mg/dL) | Glucose Recovered (mg/dL) |
|---|---|
| 100 | 99 |
| 200 | 204 |
| 300 | 292 |
| 400 | 403 |
| 500 | 473 |

Calibration Factor on COBAS MIRA 4803

The assay can also be carried out using readily apparent substitutes for the TRIS buffer such as phosphates, or other Good's buffers etc. Alternatives to ATP such as other nucleotide triphosphates are also contemplated. Alternatives to MgSO$_4$ such as manganese or other divalent metal salts are possible.

6. Determination of Creatine Kinase Activity

Creatine kinase can be determined with the following procedure using NAD analogs and NADP analogs.

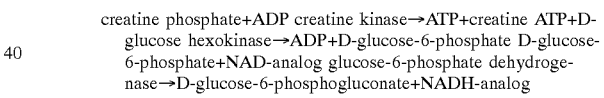

creatine phosphate+ADP creatine kinase→ATP+creatine ATP+D-glucose hexokinase→ADP+D-glucose-6-phosphate D-glucose-6-phosphate+NAD-analog glucose-6-phosphate dehydrogenase→D-glucose-6-phosphogluconate+NADH-analog In this coupled enzyme procedure the activity of creatine kinase or one of its isoforms or isoenzymes can be determined by the rate of reduction of the NAD analog in the presence of a divalent metal such as magnesium. A kit for carrying out this measurement would include, for example, thionicotinamide-NAD or thionicotinamide-NADP, 3-acetylpyridine-NAD or 3-acetylpyridine-NADP, 3-pyridinealdehyde-NAD or 3-pyridinealdehyde-NADP, a buffer, creatine phosphate, glucose, hexokinase, glucose-6-phosphate dehydrogenase, adenosine 5'-diphosphate and a divalent metal ion such as magnesium.

Alternatively, glucokinase can be substituted for hexokinase, and a sulfhydryl compound such as N-acetylcysteine can be added to the reagent to activate creatine kinase in the sample. Also other nucleotide triphosphates and divalent metal ion salts substitutions are possible.

7. Determination of Glucose-6-Phosphate Dehydrogenase Activity

Glucose-6-phosphate activity can be determined with the following procedure using NAD analogs and NADP analogs.

D-glucose-6-phosphate+NAD-analog glucose-6phosphate dehydrogenase→6-phospho-D-gluconate+NADH-analog In this reaction the activity of glucose-6-phosphate dehydrogenase activity can be determined by the rate of reduction of the NAD analog or NADP analog in the presence of a buffer and D-glucose-6-phosphate. A kit for carrying out this measurement would include, for example, a buffer, D-glucose-6-phosphate, thionicotinamide-NAD or thionicotinamide-NADP, 3-acetylpyridine-NAD or 3-acetylpyridine-NADP, and 3-pyridinealdehyde-NAD or 3-pyridinealdehyde-NADP.

8. Determination of Triglycerides

Triglycerides can be determined with the following procedure using NAD analogs.

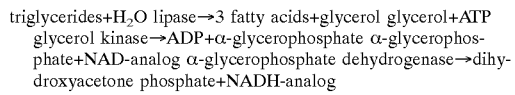

triglycerides+H₂O lipase→3 fatty acids+glycerol glycerol+ATP glycerol kinase→ADP+α-glycerophosphate α-glycerophosphate+NAD-analog α-glycerophosphate dehydrogenase→dihydroxyacetone phosphate+NADH-analog In this coupled enzyme procedure in the presence of a divalent metal such as magnesium, the quantity of NADH analog formed will be equal to the quantity of triglycerides in a sample. A kit useful for carrying out this determination would include an NAD analog such as thionicotinamide-NAD, 3-acetylpyridine-NAD, 3-pyridinealdehyde-NAD, a lipase, a divalent metal such as magnesium, adenosine 5'-triphosphate, glycerol kinase, α-glycerophosphate dehydrogenase, and a buffer. Also other nucleotide triphosphates and divalent metal substitutions are possible.

9. Determination of Bile Acids

Bile acids can be determined with the following procedure using NAD analogs or NADP analogs.

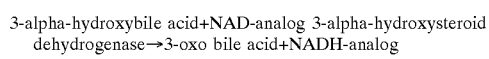

3-alpha-hydroxybile acid+NAD-analog 3-alpha-hydroxysteroid dehydrogenase→3-oxo bile acid+NADH-analog In this enzymatic procedure the quantity of NADH analog formed will be equal to the quantity of bile acids in a sample. A kit useful for carrying out this determination would include for example, an NAD analog or NADP analog such as thionicotinamide-NAD or thionicotinamide-NADP, 3-acetyl-pyridine-NAD or 3-acetylpyridine-NADP, 3-pyridinealdehyde-NAD or 3-pyridinealdehyde-NADP, 3-alpha-hydroxysteroid dehydrogenase and a buffer. A kit may also include a trapping compound such as a primary amine or primary diamine to remove the oxo-bile acid and drive the reaction in the forward direction.

10. Determination of Lactic Acid Dehydrogenase Activity

Lactic acid dehydrogenase activity can be determined with the following procedure using NAD analogs.

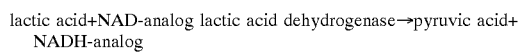

lactic acid+NAD-analog lactic acid dehydrogenase→pyruvic acid+ NADH-analog

In this reaction the activity of lactate dehydrogenase can be determined by the rate of reduction of the NAD analog in the presence of a buffer and lactic acid. A kit for carrying out this measurement would include, for example, a buffer, lactic acid and an NAD analog such as 3-propionylpyridine adenine dinucleotide, 3-isoprpionylpyridine adenine dinucleotide, or 3-butyryladenine dinucleotide. A kit may also include a trapping compound, such as a primary amine or primary diamine to remove the pyruvic acid and drive the reaction in the forward direction.

The above examples serve to provide further appreciation of the invention but are not meant in any way to restrict the effective scope of the invention.

What is claimed is:

1. A diagnostic reagent kit for measuring an analyte selected from the group consisting of: ethanol and triglycerides comprising:
   a) a cofactor selected from the group consistinig of 3-acetylpyridine-NAD, 3-acetylpyridine-NADP, 3-pyridinealdehyde-NAD and 3-pyridinealdehyde-NADP and
   b) an enzyme selected from the group consisting of glycerol kinase, alpha-glycerophosphate dehydrogenase, lipases and alcohol dehydrogenase.

2. The diagnostic kit of claim 1, further comprising a buffer.

3. A kit in accordance with claim 1 for measuring ethanol, comprising:
   a) a compound of Formula (I) selected from the group consisting of 3-acetylpyridine-NAD, 3-acetylpyridine-NADP 3-pyridinealdehyde-NAD and 3-pyridinealdehyde-NADP; and further comprising:
   b) alcohol dehydrogenase.

4. A kit in accordance with claim 1 for measuring triglycerides, comprising:
   a) a compound of Formula (I) selected from the group consisting of 3-acetylpyridine-NAD and 3-pyridinealdehyde-NAD; and further comprising:
   b) a lipase;
   c) adenosine 5'-triphosphate;
   d) glycerol kinase;
   e) α-glycerophosphate dehydrogenase; and
   f) a divalent metal ion.

5. A diagnostic reagent kit for measuring ethanol, comprising
   a) a cofactor selected from the group consisting of thionicotinamide-NAD and thionicotinamide-NADP and b) alcohol dehydrogenase.

6. A method of quantifying the presence of an analyte selected from the group consisting of ethanol and triglycerides,in a sample comprising:
   a) contacting said sample with a cofactor selected from the group consisting of 3-acetylpyridine-NAD, 3-acetylpyridine-NADP, 3pyridinealdehyde-NAD and 3-pyridinealdehyde-NADP and an enzyme selected from the group consisting of glycerol kinase, alpha-glycerophosphate dehydrogenase, lipases and alcohol dehydroggenase; and
   b) measuring the change of absorbance or fluorescence resulting from said contacting step a).

7. The method of claim 6, further comprising conducting said contacting step a) in the presence of a buffer.

8. The methode of claim 6, wherein said absorbance is measured over from about 310 to about 420 nanometers.

9. The method of claim 6, wherein said analyte is ethanol, said cofactor is 3-acetylpyridine-NAD and said enzyme is alcohol dehydrogenase.

10. The method of claim 6, wherein said analyte is ethanol, said cofactor is 3-acetylpyridine NADP and said enzyme is alcohol dehydrogenase.

11. The method of claim 6, wherein said analyte is triglycerides said cofactor is 3-acetylpyridine-NAD or 3-pyridinealdehyde-NAD and said enzyme comprises glycerol kinase, alpha-glycerophosphate dehydrogenase and a lipase.

12. A method of quantifying the presence of ethanol in a sample comprising:
   a) contacting said sample with thionicotinamide-NADP and alcohol dehydrogenase and
   b) measuring the change of absorbance or fluorescence resulting from said contacting step a).

13. The method of claim 12, wherein said absorbance is measured over from about 360 to about 450 nanometers.

* * * * *